United States Patent

Schlereth et al.

(10) Patent No.: US 8,621,947 B2
(45) Date of Patent: Jan. 7, 2014

(54) ASSEMBLY DEVICE FOR A MEASURING PROBE FOR MEASURING PROCESS VARIABLES IN A PROCESS

(75) Inventors: Rainer Schlereth, Neuss (DE); Hans-Joachim Oppermann, Gemmrigheim (DE)

(73) Assignee: Endress + Hauser Conducta Gesellschaft für Mess—und Regeltechnik mbH + Co. KG, Gerlingen (DE)

( * ) Notice: Subject to any disclaimer, the term of this patent is extended or adjusted under 35 U.S.C. 154(b) by 140 days.

(21) Appl. No.: 13/265,381

(22) PCT Filed: Mar. 30, 2010

(86) PCT No.: PCT/EP2010/054209
§ 371 (c)(1),
(2), (4) Date: Oct. 20, 2011

(87) PCT Pub. No.: WO2010/121893
PCT Pub. Date: Oct. 28, 2010

(65) Prior Publication Data
US 2012/0036948 A1 Feb. 16, 2012

(30) Foreign Application Priority Data
Apr. 21, 2009 (DE) .......................... 10 2009 002 545

(51) Int. Cl.
*G01D 11/30* (2006.01)
(52) U.S. Cl.
USPC ....................................................... 73/866.5
(58) Field of Classification Search
None
See application file for complete search history.

(56) References Cited

U.S. PATENT DOCUMENTS 4,346,611 A 8/1982 Welker
4,928,517 A * 5/1990 Fitts ................................ 73/105

FOREIGN PATENT DOCUMENTS

| CH | 521 657 | 4/1972 |
| DE | G 86 33 674.6 | 4/1987 |
| DE | 41 40 286 C2 | 6/1998 |
| DE | 10 2006 022 979 A1 | 11/2007 |
| DE | 10 2006 022 981 A1 | 11/2007 |
| EP | 0 590 290 A1 | 4/1994 |
| EP | 0 882 896 A1 | 12/1998 |
| EP | 1 156 323 A1 | 11/2001 |
| EP | 1 248 102 A1 | 10/2002 |

OTHER PUBLICATIONS

English translation of International Preliminary Report on Patentability of PCT/EP2010/054209.

* cited by examiner

*Primary Examiner* — Robert R Raevis
(74) *Attorney, Agent, or Firm* — Bacon & Thomas, PLLC

(57) ABSTRACT

An assembly device, especially a retractable assembly, for a measuring probe for measuring process variables in a process, comprising: an assembly housing with a connection system for connecting the assembly device to a process container; a tubular holder for a measuring probe, wherein the tubular holder is guided in the assembly housing axially displaceably between a measuring position in the process container and a maintenance position outside of the process container; and a damping system to damp axial shifting of the tubular holder. The damping system comprises a fluid filled, damping cylinder within the assembly housing, and a damping piston unit guided within the damping cylinder (15) in operative connection with the tubular holder.

8 Claims, 2 Drawing Sheets

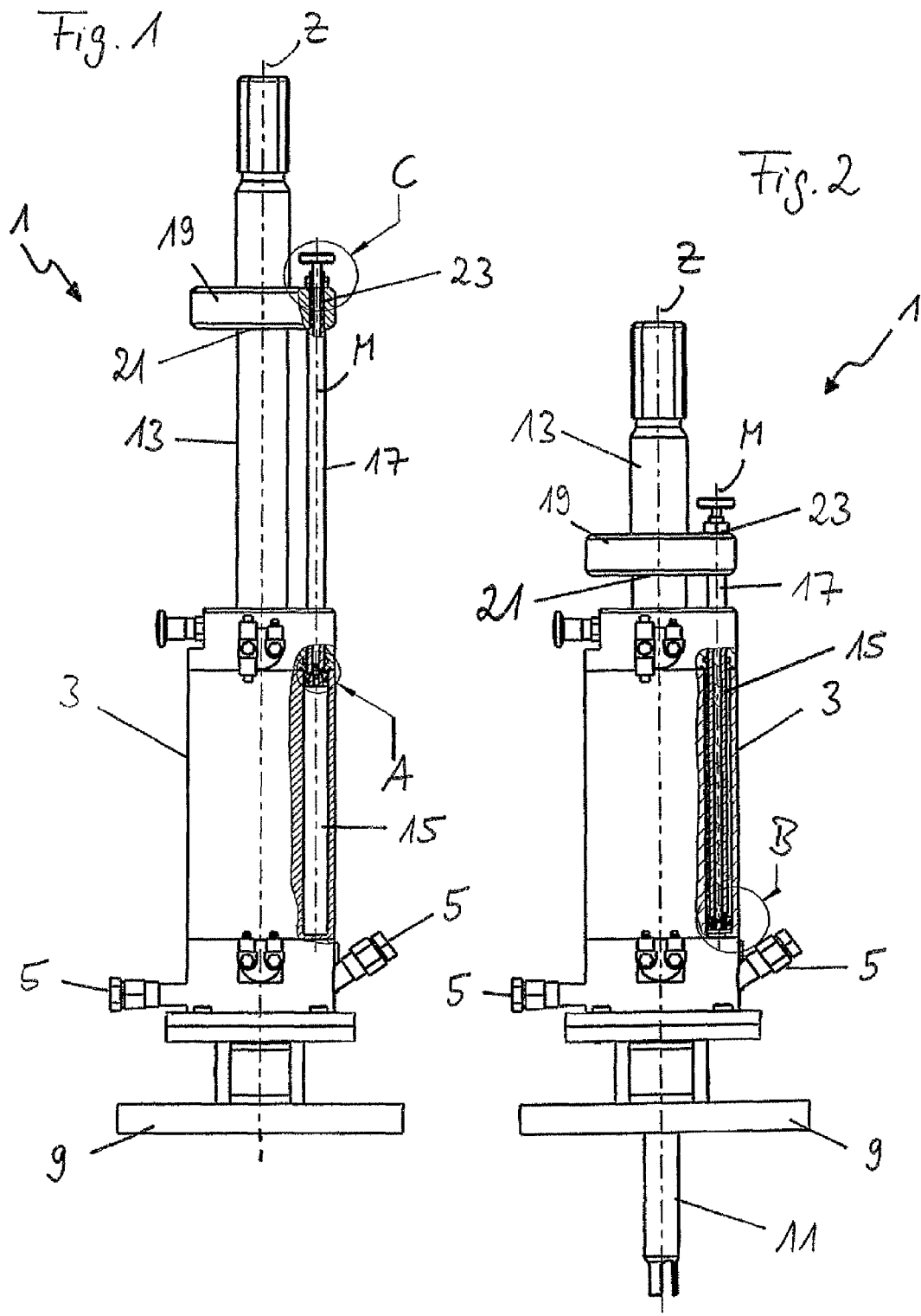

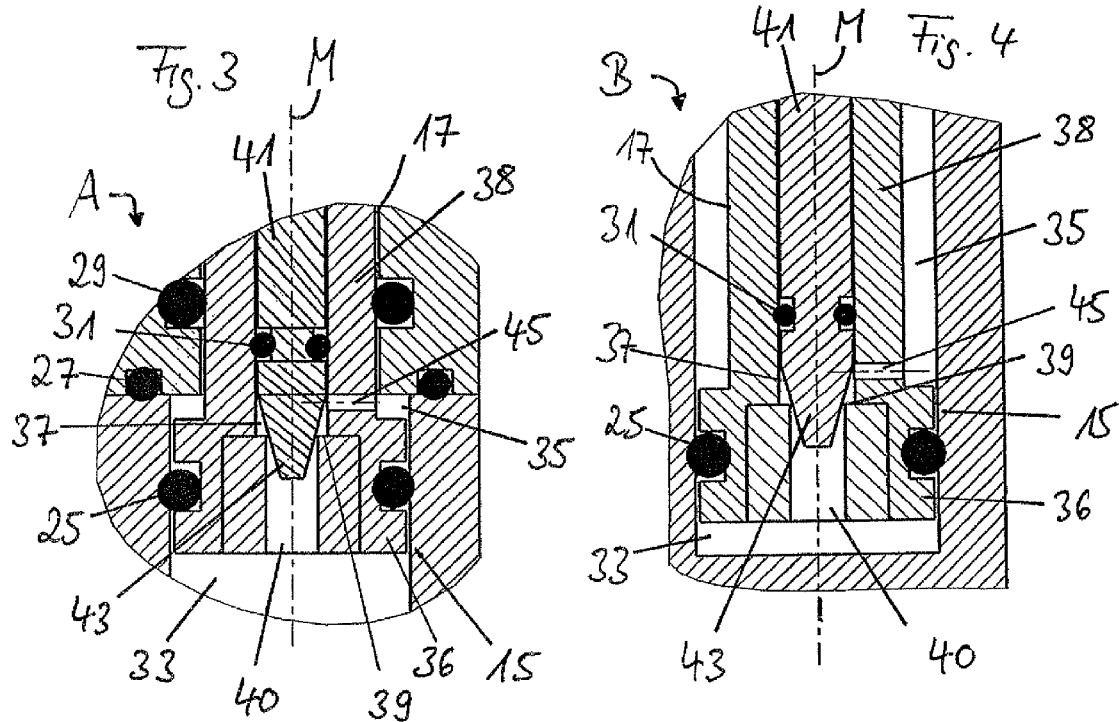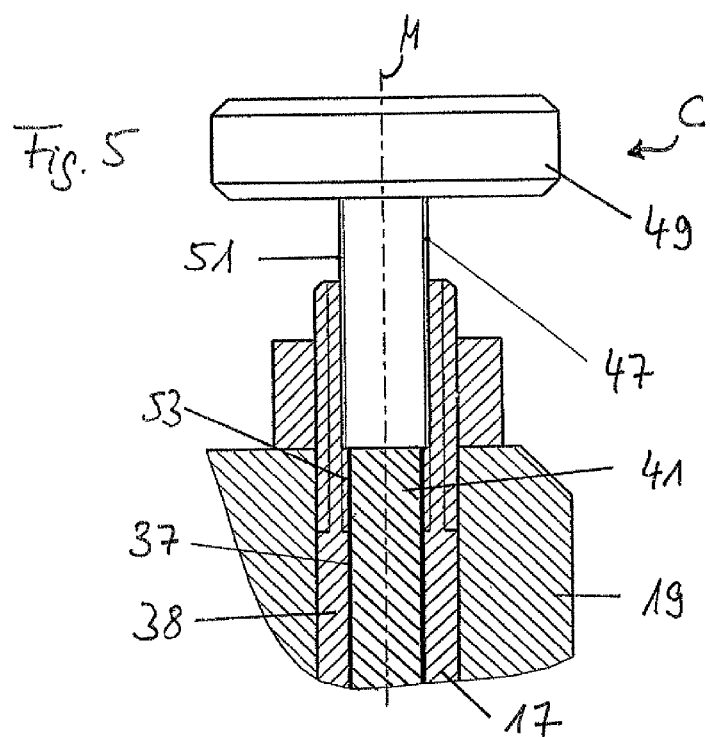

ASSEMBLY DEVICE FOR A MEASURING PROBE FOR MEASURING PROCESS VARIABLES IN A PROCESS

TECHNICAL FIELD

The invention relates to an assembly device, especially a retractable assembly, for a measuring probe for measuring process variables in a process.

BACKGROUND DISCUSSION

Assembly systems, especially retractable assemblies, which are also referred to as push rod assemblies, are widely distributed in analytical measurements technology. They serve to introduce or withdraw measuring probes, e.g. sensors, into a process without interrupting the process. For this, the measuring probe is usually accommodated in a tubular holder, which is shiftably accommodated within an assembly housing of the assembly device and is guided between a measuring position and a maintenance position. The shifting of the tubular holder with the measuring probe can occur manually or automatically, for example, with the assistance of a pneumatic drive system. A pneumatic drive system for shifting the holder for the measuring probe can comprise a pneumatic cylinder and a movable, compressed air driven, piston therein, with which the tubular holder for the measuring probe is connected directly or via one or more connecting parts.

The assembly housing has a connection system, for example, a flange, to connect the assembly device to a process container. A calibration and/or cleaning chamber, into which the measuring probe can be drawn to a maintenance position, can be provided within the assembly housing in order to clean and/or calibrate the measuring probe.

In order to seal off the calibration and/or cleaning chamber from the process to be monitored, internal sealing rings are frequently arranged on the guide of the tubular holder in the region of the calibration chamber in the assembly housing; the sealing rings lie against smooth sealing surfaces on the process side end of the tubular holder.

Here and in the following, the side of the assembly device, on which the connection system for connecting to a process container is placed, is referred to as "process side". Correspondingly, the direction along the central longitudinal axis of the assembly device toward the connection system is referred to as "on the process side". The direction set counter to the process side direction is referred to as "facing away from the process."

The firm of Endress+Hauser offers such assembly systems under the "Cleanfit" mark, examples of these are CleanFit S, CPA 471, CPA 472 and 472D, CPA 473, CPA 474 and CPA 475. The movement of the holder for the measuring probe occurs in an axial direction in these assembly systems, i.e. along a central axis of the assembly device. The movement occurs via a pneumatic drive automatically or by means of a manual actuation. In order to achieve a smooth approach of the retractable assembly to the particular position and especially to avoid damage to the measuring probe by too abrupt stopping in the measuring position or maintenance position, the axial movement of the measuring probe holder is damped with the assistance of a supplemental throttle element, which is mounted in the air supply of the pneumatic drive of the respective desired movement direction, namely in the measuring position or the maintenance position in assemblies with pneumatic drive systems.

As a supplemental component, such a throttle element is, however, on one hand, relatively expensive, especially because a throttle element is required for each movement direction, and on the other hand, has the disadvantage that it is only suitable in connection with the pneumatic drive for damping the movement of the measuring probe or the measuring probe holder.

SUMMARY OF THE INVENTION

It is the object of the invention to provide an assembly device of the type initially named that avoids the disadvantages of the state of the art. The shifting movement of the holder for the measuring probe should especially be effectively damped with as simple a construction of the assembly device and the damping means as possible.

This object is achieved by an assembly device, especially a retractable assembly, for a measuring probe for measuring process variables in a process, comprising:
an assembly housing with a connection system for connecting the assembly device to a process container; a tubular holder for a measuring probe, wherein the tubular holder is guided in the assembly housing axially displaceably between a measuring position in the process container and a maintenance position outside of the process container; and
a damping system to damp axial shifting of the tubular holder, wherein the damping system comprises a fluid filled, damping cylinder within the assembly housing, and a damping piston unit guided within the damping cylinder in operative connection with the tubular holder. An operative connection between the damping piston unit and the holder is here understood to mean that a damping piston unit and a holder are mechanically coupled in such a manner that with a movement, especially a shifting, of the tubular holder, the damping piston unit mandatorily moves likewise, especially is shifted within the damping cylinder. The operative connection can especially be a rigid connection between the damping piston unit and the holder, especially via one or a number of connecting parts.

Through the operative connection between the damping piston unit and the axially shiftable, tubular holder in the assembly housing, the movement of the damping piston unit within the fluid filled, damping cylinder thus is directly coupled to the axial movement of the holder for the measuring probe when shifting the measuring probe between a measuring position and a maintenance position. Since the damping piston unit is guided within a fluid filled, damping cylinder, a damping effect results due to the flow resistance of the fluid counteracting the movement of the damping piston unit; the damping effect, in turn, affects the movement of the holder directly through the operative connection between the damping piston unit and the measuring probe holder. In this way, an effective damping of the axial shifting movement of the tubular holder is achieved. Thus, no additional components, such as for example, one or a number of throttles acting on a pneumatic drive of the assembly device, are required for damping the shifting movement. Since the damping effect is not achieved by means of such a throttling of a pneumatic control as in the state of the art, the damping system described here is suitable for both automatically, especially pneumatically, operated assembly systems as well as for manually operated assembly systems. Furthermore, only one damping system is required for the shifting movement in both directions since the damping effect due to the flow resistance of the fluid occurring with the movement of the damping piston unit occurs in both directions.

In a preferred embodiment, the damping piston unit has a fluid passageway, which connects a first volume of the damping cylinder to a second volume of the damping cylinder. In this way, fluid from the first volume can flow into the second volume or in the reverse direction with the movement of the damping piston unit through the damping cylinder. The fluid passageway preferably has a significantly smaller cross section, at least sectionally, than the damping cylinder so that through the braking action of the fluid flowing through this cross sectional restriction, a noticeable damping of a stroke movement of the damping piston unit is achieved. The cross sectional ratio, depending on the viscosity of the fluid in the damping cylinder can be set in order to achieve the desired damping effect.

In an alternative embodiment, a fluid passageway extending within the damping piston unit can be omitted by having the damping piston unit only partially seal fluid tightly on its periphery with the inner wall of the damping cylinder so that fluid from the first volume can flow to the second volume between the damping piston unit and the inner wall of the damping cylinder surrounding the damping piston unit.

The cross section of the fluid passageway can be adjusted by means of a valve element in order to set the flow resistance, with which the fluid opposes the movement of the damping piston unit in a transition from the first to the second volume or a transition from the second to the first volume. In this way, the damping effect on the movement of the damping piston unit within the damping cylinder can be varied and set as desired.

The damping piston unit can comprise a damping piston rod with a first diameter and an adjacent piston with a second diameter on a process side end of the damping piston rod, wherein the first diameter is smaller than the second diameter, and wherein the first volume borders the process side, end face of the piston and the second volume borders the rear side of the piston facing away from the process.

The valve element mentioned can be formed by a bore section, especially a constricted bore section of a bore, especially a cylindrical bore, extending axially within the damping piston unit and a spindle, especially an at least sectionally cone or frustoconically shaped spindle, which is at least sectionally continuously tapering, protruding into the bore section, wherein the spindle closes the bore section except for an annular opening, which is also referred to as an annular gap in the following, wherein the cross section of the annular opening is adjustable by shifting the spindle into the bore section or out of the bore section.

The bore section can be a constricted section of the axial bore extending within the damping piston unit, for example. If the axial bore constricts in a stepwise fashion, for example, i.e. abruptly from a first to a second, smaller, cross section, the conical spindle can be so arranged that its continuously tapering section protrudes from the bore section with the first cross section into the constricted bore section with the smaller cross section. An annular gap is formed between the edge surface of the spindle, which, for example, can be embodied as a conical surface or a frustoconical surface, and the step formed by the constriction of the bore, referred to as a "step shaped constriction" in the following for purposes of simplicity.

The spindle can be placed on a process side end of a pin guided within the damping piston rod, for example, extending in the axial bore within the damping piston unit, wherein the pin or a pin extension is secured to the damping piston rod by an external thread, which interacts with an internal thread of the damping piston rod. The screw thread connection between the pin or the pin extension and the damping piston rod permits a shifting of the spindle in an axial direction. By turning the pin in the process side direction, the spindle is shifted, for example, into the constricted bore section within the damping piston, which leads to a reduction of the annular opening and therewith to a decrease of the fluid passage cross section. Turning the pin in a direction away from the process leads correspondingly to a shifting of the spindle out of the constricted bore section, which leads to an increase in the annular opening and correspondingly an increase in the cross section of the fluid passageway.

The first volume of the damping cylinder can be connected to the second volume of the damping cylinder via the axial bore within the damping piston and via a radial bore, which has a first exit into the axial bore and a second exit into the second volume of the damping cylinder.

An operative connection between the damping piston unit and the tubular holder for the measuring probe can be achieved, for example, in that the tubular holder or a holder extension connected to the tubular holder in an end region has a connecting piece, e.g. a plate with a first passageway, in which the tubular holder is secured, and which has a second passageway opposite the first shifted in a radial direction relevant to the central axis of the assembly device, which coincides with the longitudinal axis of the tubular holder; the damping piston rod or an extension of the damping piston rod is secured in the second passageway. Through the radial offset of the damping piston unit relative to the tubular holder for the measuring probe, the damping piston unit simultaneously acts as a twist preventer for the measuring probe. Since the damping piston unit is tightly held in an end region of said plate and in the damping cylinder at its other end region, a twist of the tubular holder around its rotational axis is suppressed. This is especially advantageous when the measuring probe held in the assembly device is not rotationally symmetric, when thus its orientation relative to the rotational axis of the probe holder plays a role in the quality of the measurement results. This is the case, for example, with ISFET-pH sensors or other semiconductor sensors as well as with rotationally asymmetric optical probes, such as, for example, turbidity sensors or photometric measuring sensors. Especially for the case when one of these measuring probes is arranged in a flowing medium, its orientation relative to the flow direction plays an important role in the quality of the measurement results.

BRIEF DESCRIPTION OF THE DRAWINGS

The invention will now be explained in greater detail based on the example of an embodiment shown in the drawing, the figures of which show as follows:

FIG. 1 is an assembly device with a measuring probe holder in the maintenance position;

FIG. 2 shows the assembly device of FIG. 1 with the measuring probe holder in the measuring position;

FIG. 3 is an enlarged representation of section A of FIG. 1, in which the process side, end region of the damping piston unit is seen in a stop position in the end region of the damping cylinder facing away from the process;

FIG. 4 is an enlarged representation of section B of FIG. 2, in which the process side, end region of the damping piston unit is seen in a stop position in the process side, end region of the damping piston unit;

FIG. 5 is an enlarged representation of section C of FIG. 1, in which the end region of the damping piston unit facing away from the process is seen.

DETAILED DISCUSSION IN CONJUNCTION WITH THE DRAWINGS

FIG. 1 shows an assembly device 1 with an assembly housing 3; the measuring probe (not presented) is located in the maintenance position within a cleaning and calibration chamber within assembly housing 3. FIG. 2 shows same assembly device 1 in the measuring position with holder 11 for the measuring probe (not shown) extended. Calibration or cleaning liquid can be transferred through the input and output 5 into and back out of the calibration or cleaning chamber.

Assembly device 1 has a flange as a connection system 9; assembly device 1 can be fixed to a process vessel (not illustrated), a pipe for example, by the flange. Holder 11 for the measuring probe is secured to a holder extension 13 by a screwed connection or a bayonet closure (not shown in FIGS. 1 and 2), for example. Holder 11, as well as holder extension 13, are axially, i.e. in the direction of the central axis Z of assembly device 1, displaceably guided into assembly housing 3. Central axis Z coincides with the longitudinal axis of holder 11 or holder extension 13. The assembly housing 3, probe holder 11 and holder extension 13 can be constructed in a known manner, such as described, for example, in DE 102006010810 A1, DE 102007035918 B3 or DE 102006022981 A1.

A damping cylinder 15, which can be embodied, for example, as a blind bore in the wall of assembly housing 3, is arranged within assembly housing 3. A damping piston unit 17 is applied in damping cylinder 15 in such a manner that it can execute stroke movements along the central axis M of damping cylinder 15. Holder extension 13 is accommodated in a first passageway 21 of the plate 19. Plate 19 has a second passageway 23, which is shifted in a radial direction relative to the first passageway 21, i.e. in a direction perpendicular to central axis Z. Damping piston unit 17 is secured in this second passageway 23. In this manner, an operative connection in the form of a rigid mechanical coupling between holder 11 for the measuring probe and damping piston unit 17 results via holder extension 13. If holder extension 13 is shifted, together with holder 11, in the direction of central axis Z of assembly device 1 within assembly housing 3, an unavoidable simultaneous movement of damping piston unit 17 in the same direction, in which holder extension 13 and, thus, holder 11 for the measuring probe move, along its central axis M, which is parallel to central axis Z, occurs.

FIG. 3 shows an enlargement of section A of FIG. 1 and FIG. 4 shows an enlargement of section B of FIG. 2. The end of damping cylinder 15 facing away from the process as well as the process side region of damping piston unit 17 with the measuring probe retracted to the maintenance position are shown in FIG. 3. FIG. 4 shows the process side end of damping cylinder 15 as well as the process side region of damping piston unit 17 abutting the measuring position of the measuring probe on the process side end of damping cylinder 15. Damping cylinder 15 has a fluid filled hollow space, which is sealed fluid tightly against the environment by means of the sealing rings 25, 27 and 29. The fluid contained in damping cylinder 15 cannot escape into the environment. Damping piston unit 17 comprises a damping piston rod 38 and a piston 36 on the process side, end region of the piston rod. Piston 36 is provided with an annular groove for accommodating the sealing ring 25. Sealing ring 25 lies fluid tightly against the smooth inner wall of damping cylinder 15. Piston of damping piston unit 17 divides, thus, the internal volume of damping cylinder 15 into a first volume 33 between the process side cylindrical base surface of damping cylinder and the process side, end face of piston 36 and into a second volume 35 on the side of piston 36 lying opposite, which is bordered by the end of damping cylinder 15 facing away from the process with seal 29, the inner wall of damping cylinder 15, the cylinder lateral surface of damping piston rod 38, and the rear side of piston 36 extending radially around damping piston rod 38.

Damping piston unit 17 has a traversing axial bore 37, i.e. extending along central axis M of damping piston unit 17; a pin 41 is guided within bore 37; pin 41 transforms into a spindle 43 of frustoconical geometry in its process side, end region. In the region of piston 36 of damping piston unit 17, axial bore 37 has a stepped constriction 39, i.e. axial bore goes abruptly from a bore section with a first cross section to a second bore section 40 with a smaller cross section. The frustoconical shaped spindle 39 protrudes into tapered bore section 40 of axial bore 37 in such a manner that only a narrow annular gap remains between step 39 and the cone wall of the spindle 43. On the side of the piston facing away from the process, axial bore 37 is connected to the second volume 35 of damping cylinder 15 by a radial, i.e. extending perpendicularly to central axis M, bore 45. Pin 41 has an annular groove, in which sealing ring 31 is accommodated, above radial bore 45. Sealing ring 31 lies against the smooth inner wall of axial bore 37 and so seals the bore interior fluid tightly against the environment.

With a movement of damping piston unit 17 in the process side direction, i.e. into damping cylinder 15, fluid is squeezed from first volume 33 and flows into second volume 35 of damping cylinder 15 on the side of piston 36 facing away from the process via axial bore 37, via the annular gap formed between stepped constriction 39 and the conical surface of spindle 43 and via radial bore 45. Due to the small cross section of the annular gap between spindle 43 and step like constriction 39, the fluid opposes the movement of damping piston unit 17 with a high flow resistance, which brakes the movement of damping piston unit 17. With a movement of the damping piston unit in the opposite direction fluid is correspondingly squeezed from second volume 35 of damping cylinder 15 into first volume 33 of damping cylinder 15 via radial bore 45, the annular gap between spindle 43 and stepped constriction 39 and via axial bore 37. Again, there results a damping of the stroke movement of damping piston unit 17 due to the high flow resistance, with which the fluid opposes the piston movement due to the annular gap.

The cross section of the annular gap can be varied in the example of an embodiment shown here and selected depending on the viscosity of the fluid and the desired damping intensity.

FIG. 5 shows an enlargement of section C of FIG. 1, in which a section of plate 19 and of damping piston unit 17 secured therein, is presented. Pin 41 guided within damping piston rod 38 is accommodated in a pin extension 47 on its end facing away from the process. Pin extension 47 is provided with a knurled nut 49 on its end facing away from the process. Pin extension 47 has, moreover, an external thread 51, which interacts with an internal thread 53 of damping piston rod 38. By rotating knurled nut 49, pin extension 43 can correspondingly be rotated out from damping piston rod 38 or rotated into damping piston rod 38. This effects an axial movement of pin 41 into axial bore 37, i.e. a movement in the process side direction or a movement out from axial bore 37, i.e. a movement in a direction facing away from the process. Correspondingly, the distance between the conical surface of spindle 43 and step like constriction 39 decreases in a movement of pin 41 into the axial bore or increases in a movement out from the axial bore. The cross section of the annular gap between spindle 43 and stepped constriction 39 correspondingly lessens with a decreasing separation; the cross section of the annular gap correspondingly enlarges with an increase in the separation. In this way, the strength of the flow resistance, which counteracts a movement of damping piston unit 17 within damping cylinder 15, can be set.

Many liquids and gases are suitable as the fluid, in principle. In the simplest case, air from the environment under atmospheric conditions is enclosed in the construction of the damping cylinder and the damping piston unit. However, a damping liquid can equally be enclosed in the damping cylinder during manufacture.

The invention claimed is:

1. An assembly device, for a measuring probe for measuring process variables in a process, comprising:
   an assembly device housing with a connection system for connecting the assembly device to a process container;
   a tubular holder for a measuring probe, wherein said tubular holder is guided in said assembly device housing axially displaceably between a measuring position in the process container and a maintenance position outside of the process container; and
   a damping system to damp axial shifting of said tubular holder, wherein:
   said damping system comprises a fluid filled, damping cylinder within said assembly device housing, and a damping piston unit guided within said damping cylinder in operative connection with said tubular holder.

2. The assembly device as claimed in claim 1, wherein:
   shifting of said tubular holder simultaneously effects shifting of said damping piston unit within said damping cylinder through the operative connection between said tubular holder and said damping piston unit.

3. The assembly device as claimed in claim 1, wherein:
   said damping piston unit has a fluid passageway, which connects a first volume of said damping cylinder to a second volume of said damping cylinder.

4. The assembly device as claimed in claim 3, wherein:
   the cross section of said fluid passageway is adjustable by means of a valve element in order to set the amount of fluid flow from said first volume to said second volume.

5. The assembly device as claimed in claim 4, wherein:
   said valve element comprises an at least sectionally continuously tapering spindle, wherein said fluid passageway comprises a bore section of a bore extending axially within said damping piston unit;
   said spindle protrudes into said bore section and closes this except for an annular opening in said fluid passageway; and
   the cross section of said annular opening is adjustable by shifting said spindle into said bore section or out from said bore section.

6. The assembly device as claimed in claim 5, wherein:
   said damping piston unit comprises a damping piston rod;
   said spindle is placed on an end of a guided pin in said axial bore within said damping piston rod; and
   said pin or a pin extension has a first screw thread, which interacts with a second screw thread, complementary to the first screw thread, of said damping piston rod.

7. The assembly device as claimed in claim 6, wherein:
   said first volume of said damping cylinder is connected to said second volume of said damping cylinder via said axial bore within said damping piston rod and via a radial bore, which has a first exit into said axial bore and a second exit into said second volume of said damping cylinder, therefore defining said fluid passageway.

8. The assembly device as claimed in claim 6, wherein:
   said tubular holder or a holder extension connected to said tubular holder is secured in a first passageway of a connecting piece; and
   said connecting piece has a second passageway shifted relative to the first passageway in a radial direction relative to the longitudinal axis of said tubular holder and said damping piston rod or an extension of said damping piston rod is secured in said second passageway.

* * * * *